US00PP13049P2

(12) United States Plant Patent
Head et al.

(10) Patent No.: US PP13,049 P2
(45) Date of Patent: Oct. 1, 2002

(54) MAGNOLIA TREE NAMED 'SOUTHERN CHARM'

(75) Inventors: Robert Harold Head, Seneca, SC (US); Lisa Jones Head, Seneca, SC (US); William Alan Head, Walhalla, SC (US)

(73) Assignee: Head Ornamentals, Inc., Seneca, SC (US)

( * ) Notice: Subject to any disclaimer, the term of this patent is extended or adjusted under 35 U.S.C. 154(b) by 0 days.

(21) Appl. No.: 09/840,807

(22) Filed: Apr. 25, 2001

(51) Int. Cl.[7] ..... A01H 5/00
(52) U.S. Cl. ..... Plt./223

(58) Field of Search ..... Plt./223

(56) References Cited

U.S. PATENT DOCUMENTS

PP11,612 P * 10/2000 Strickland ..... Plt./223

* cited by examiner

*Primary Examiner*—Bruce R. Campell
*Assistant Examiner*—W C Baker
(74) *Attorney, Agent, or Firm*—C. A. Whealy

(57) ABSTRACT

A distinct cultivar of Magnolia plant named 'Southern Charm', characterized by its compact, upright, narrow pyramidal, and uniform plant habit; freely-branching habit; upright lateral branch orientation; dark green leaves; and rapid growth rate.

2 Drawing Sheets

BOTANICAL CLASSIFICATION

*Magnolia grandiflora.*

BACKGROUND OF THE INVENTION

The present Invention relates to a new and distinct cultivar of Magnolia tree, botanically known as *Magnolia grandiflora*, and hereinafter referred to by the name 'Southern Charm'.

The new Magnolia originated from a cross made by the Inventors of two unidentified selections of *Magnolia grandiflora*, not patented. The new Magnolia was selected as a single plant from the resulting progeny by the Inventors in a controlled environment in Seneca, S.C., in 1985.

Asexual reproduction of the new cultivar by stem cuttings taken in Seneca, S.C. since July, 1998, has shown that the unique features of this new Magnolia are stable and reproduced true to type in successive generations.

SUMMARY OF THE INVENTION

Trees of the cultivar Southern Charm have not been observed under all possible environmental conditions. The phenotype may vary somewhat with variations in environment and culture such as temperature, light intensity, daylength, water status, and/or fertilizer rate or type without, however, any variance in genotype.

The following traits have been repeatedly observed and are determined to be the unique characteristics of 'Southern Charm'. These characteristics in combination distinguish 'Southern Charm' as a new and distinct cultivar:

1. Compact, upright, narrow pyramidal, and uniform plant habit.
2. Freely-branching habit, dense trees.
3. Upright lateral branch orientation.
4. Dark green leaves.
5. Rapid growth rate.

Trees of the new Magnolia differ from trees of the parent selections primarily in plant form.

Trees of the Magnolia can be compared to trees of the Magnolia cultivar Little Gem, not patented. In side-by-side comparisons conducted by the Inventors in Seneca, S.C., trees of the new Magnolia differed from trees of the cultivar Little Gem in the following characteristics:

1. Trees of the new Magnolia are more compact and more narrow than trees of Little Gem.
2. Trees of the new Magnolia are more freely branching and are denser than trees of Little Gem.
3. Trees of the new Magnolia have stronger and more upright lateral branches than trees of Little Gem.
4. Trees of the new Magnolia start flowering during the third year's growth whereas trees of Little Gem start flowering during the first year's growth.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Magnolia.

The photograph on the first sheet comprises a side perspective view of a typical tree of 'Southern Charm'.

The photograph on the seond sheet comprises a close-up view of typical flowering branches of 'Southern Charm'.

DETAILED BOTANICAL DESCRIPTION

In the following description, color references are made to The Royal Horticultural Society Colour Chart except where general terms of ordinary dictionary significance are used. The photographs and detailed botanical description were taken in August on trees grown for four years in 75-liter containers in an open production nursery in Seneca, S.C.

with average day temperatures of 33° C. and average night temperatures of 20° C.

Botanical classification: *Magnolia grandiflora* cultivar Southern Charm.

Parentage:

*Female parent.*—Unidentified selection of *Magnolia grandiflora*, not patented.

*Male parent.*—Unidentified selection of *Magnolia grandiflora*, not patented.

Propagation:

*Type cutting.*—Stem cuttings.

*Time to initiate roots, summer.*—About 90 days at 32° C.

*Time to initiate roots, winter.*—About 120 days at 18° C.

*Time to produce a rooted cutting, summer.*—About 180 days at 32° C.

*Time to develop roots, winter.*—About 240 days at 18° C.

*Root description.*—Primary roots: Thick, fleshy, coarse. Secondary roots: Thinner than primary roots, fleshy, fibrous. Color: 158A. Habit: Freely branching.

Plant description:

*Form.*—Evergreen broadleaf tree; relatively compact, upright, narrowly pyramidal, and uniform plant habit. Freely branching; pruning is usually not required. Rapid growth rate.

*Plant height.*—About 2 meters.

*Plant diameter.*—About 75 cm.

*Vigor.*—Vigorous.

*Lateral branches.*—Length: About 12.4 cm. Diameter: About 5.7 mm. Internode length: About 1.9 cm. Aspect: About 35 to 40° from vertical. Strength: Very strong, stocky. Texture: Young stems, smooth; with development, dense brown pubescence, pannose. Color: Young: 137B. Mature with pubescence: 200C.

*Foliage description.*—Leaves simple, generally symmetrical and long-persisting; alternate. Length: About 8 to 13 cm. Width: About 3.5 to 7.5 cm. Shape: Obelliptic to obovate. Apex: Obtuse to mucronulate. Base: Equilateral cuneate to rounded. Margin: Entire; revolute with one side more curled than the other. Texture: Coriaceous. Upper surface: Smooth, with depressed venation. Lower surface: Parrose. Venation pattern: Costate. Color: Young foliage, upper surface: 137A. Young foliage, lower surface: 166B. Mature foliage, upper surface: 139A; venation, 146C. Mature foliage, lower surface: 175A; venation, 175A. Petiole length: About 1.8 cm. Petiole diameter: About 2.8 mm. Petiole color: 175A.

Flower description:

*Flower type and habit.*—Solitary terminal flowers facing mostly upward. Flowers not persistent. About 15 to 20 flowers per tree.

*Natural flowering season.*—Late spring until fall, May to October, in Seneca, S.C. Plants start flowering during the third year of growth.

*Flower longevity on the plant.*—About 3 days.

*Flower longevity as a cut flower.*—About 2 days.

*Fragrance.*—Very fragrant, typical of species.

*Flowers.*—Appearance: Cup-shaped, three-parted. Diameter: About 13.5 cm. Depth (height): About 6.5 cm.

*Flower buds* (*showing color*).—Length: About 7 cm. Diameter: About 2.5 cm. Shape: Conical. Color: 155B.

*Tepals.*—Arrangement/appearance: Three whorls with three tepals each, cupped. Length: About 8 cm. Width: About 3.5 to 6 cm. Shape: Outer tepals: Oval. Inner tepals: Obovate. Apex: Rounded to obtuse with emargination. Margin: Entire. Texture, both surfaces: Thick, smooth. Color: Upper surface, when opening and fully opened: 155A; with subsequent development, 159C. Lower surface, when opening and fully opened: 155A.

*Peduncles.*—Length: About 2.5 cm. Diameter: About 7 mm. Strength: Very strong. Color: 166C.

*Reproductive organs.*—Stamens: Quantity: About 228 per flower. Anther shape: Oblong with blunt tips. Anther length: About 1.2 cm. Anther width: About 2 mm. Anther height: About 1 mm. Anther color: 10D, towards base, 46A. Pollen amount: Abundant. Pollen color: 16C. Pistils: Quantity: About 56 per flower. Pistil length: About 1 cm. Stigma shape: Hook-shaped. Stigma color: 150A. Style length: About 3 mm. Style color: 160A. Ovary color: 160A.

*Seed.*—Quantity: About 20 seeds per fruiting cone. Length: About 9 mm. Diameter: About 5 mm. Color: 44A.

*Fruits.*—Type: Schizocarp, cone. Quantity: About 8 to 10 fruit per tree. Length: About 5.1 cm. Diameter: About 3.8 cm. Texture: Woody, covered with pannose hairs. Color: 146B.

Disease/pest resistance: Trees of the new Magnolia have been noted to be resistant to pathogens or pests common to Magnolia.

Temperature tolerance: Trees of the new Magnolia have not been observed to be tolerant to temperatures from −18 to 40° C.

It is claimed:

1. A new and distinct cultivar of Magnolia plant named 'Southern Charm', as illustrated and described.

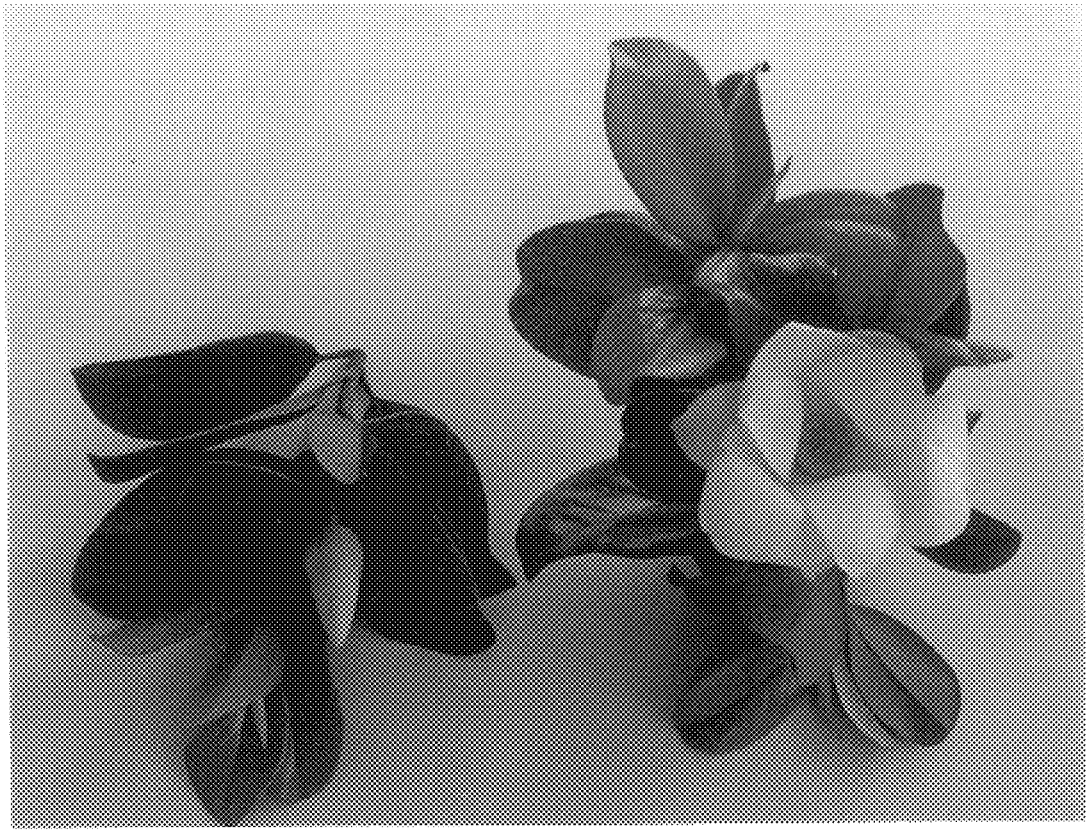

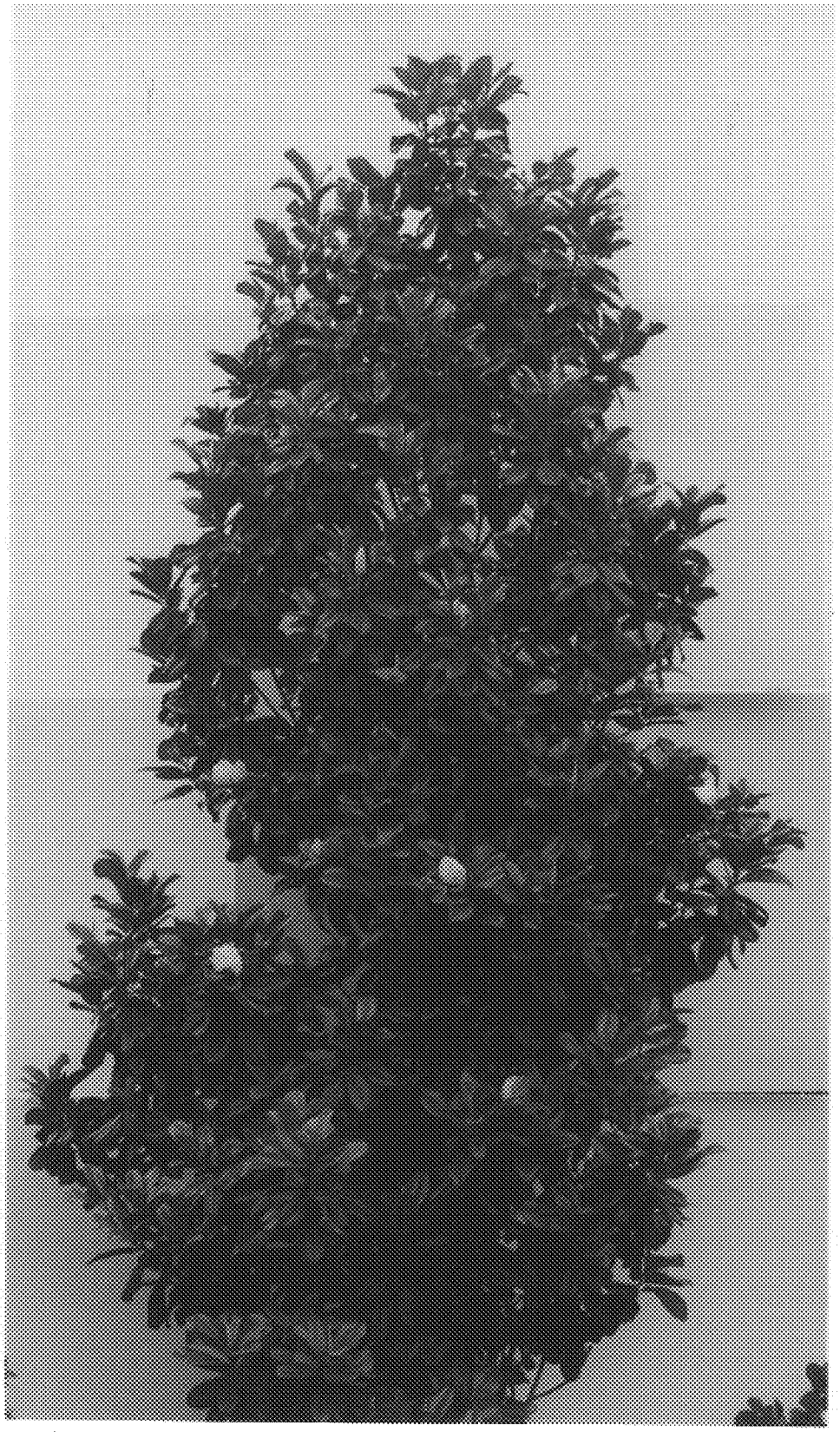

* * * * *